US012589066B2

(12) United States Patent
Da Silva et al.

(10) Patent No.: US 12,589,066 B2
(45) Date of Patent: Mar. 31, 2026

(54) COSMETIC COMPOSITION CONTAINING AN EXTRACT FROM OPUNTIA FICUS INDICA

(71) Applicant: Weleda AG, Arlesheim (CH)

(72) Inventors: Alissa Karyne Da Silva, Aesch (CH); Katarzyna Hänni-Ciunel, Magden (CH); Daniel Heizler, Basel (CH); Alicia Idoux, Bättwil (CH); Hélène Thérèse Anne Kapfer, Saint Louis (FR); Meike Schmitt, Emmendingen (CH)

(73) Assignee: WELEDA AG, Arlesheim (CH)

( * ) Notice: Subject to any disclaimer, the term of this patent is extended or adjusted under 35 U.S.C. 154(b) by 622 days.

(21) Appl. No.: 17/773,066

(22) PCT Filed: Nov. 2, 2020

(86) PCT No.: PCT/EP2020/080712
§ 371 (c)(1),
(2) Date: Apr. 29, 2022

(87) PCT Pub. No.: WO2021/084136
PCT Pub. Date: May 6, 2021

(65) Prior Publication Data
US 2024/0139094 A1 May 2, 2024

(30) Foreign Application Priority Data
Nov. 1, 2019 (EP) ..................................... 19206753

(51) Int. Cl.
*A61K 36/00* (2006.01)
*A61K 8/9789* (2017.01)
*A61Q 19/00* (2006.01)
(52) U.S. Cl.
CPC .......... *A61K 8/9789* (2017.08); *A61Q 19/007* (2013.01)
(58) Field of Classification Search
CPC ...................................................... A61K 8/042
See application file for complete search history.

(56) References Cited

U.S. PATENT DOCUMENTS

| | | | |
|---|---|---|---|
| 7,722,904 B2 | 5/2010 | Schneider et al. | |
| 10,890,202 B2 | 1/2021 | Braun | |
| 2014/0147532 A1* | 5/2014 | Yun ........................ | A61K 36/33 424/767 |
| 2018/0140537 A1 | 5/2018 | Margnat, Jr. | |

FOREIGN PATENT DOCUMENTS

| | | | |
|---|---|---|---|
| CN | 105997747 A | * | 10/2016 |
| KR | 10-2003-0023398 A | | 3/2003 |
| KR | 10-2008-0029035 A | | 4/2008 |
| KR | 10-2013-0032420 A | | 4/2013 |
| WO | 2010/081839 A1 | | 7/2010 |

OTHER PUBLICATIONS

Definition of aqueous from Dictionary.com, accessed on Jan. 10, 2025, pp. 1-5 (Year: 2025).*
Anonymous: "HPC2_2017", Mar. 1, 2017 (Mar. 1, 2017), p. 25, XP055686377.
Damasceno et al., "Use of Opuntia ficus-indica Mill extracts from Brazilian Caatinga as an alternative of natural moisturizer in cosmetic formulations" Brazilian Journal of Pharmaceutical Sciences, vol. 52, No. 3, 2016, pp. 459-470.
European Search Report for EP Patent Application No. 19206753.6, Issued on May 4, 2020, 7 pages.
International Preliminary Report on Patentability received for PCT Patent Application No. PCT/EP2020/080712, mailed on Feb. 11, 2022, 13 pages (6 pages of English Translation and 7 pages of Original Document).
International Search Report and Written Opinion received for PCT Patent Application No. PCT/EP2020/080712, mailed on Feb. 24, 2021, 13 pages (3 pages of English Translation and 10 pages of Original Document).

* cited by examiner

*Primary Examiner* — Qiuwen Mi
(74) *Attorney, Agent, or Firm* — Faegre Drinker Biddle & Reath LLP

(57) ABSTRACT

The invention relates to a cosmetic composition containing a hydrocolloidal extract of *Opuntia ficus indica*, wherein mucilages are selectively enriched. Furthermore, the invention relates to a hydrocolloidal extract of *Opuntia ficus indica*, a process for its preparation, and its use, in particular in cosmetics.

10 Claims, 2 Drawing Sheets

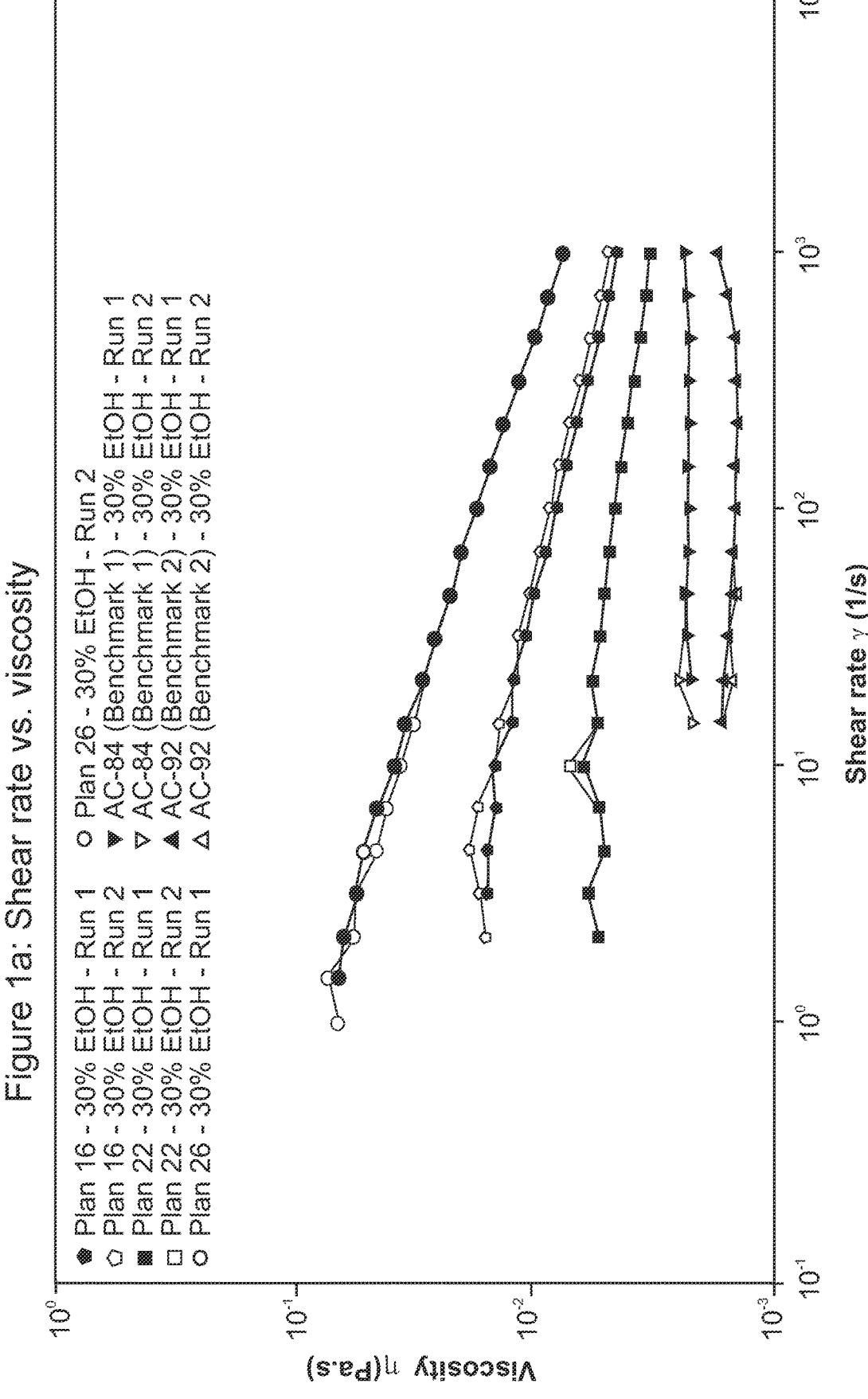
Figure 1a: Shear rate vs. viscosity

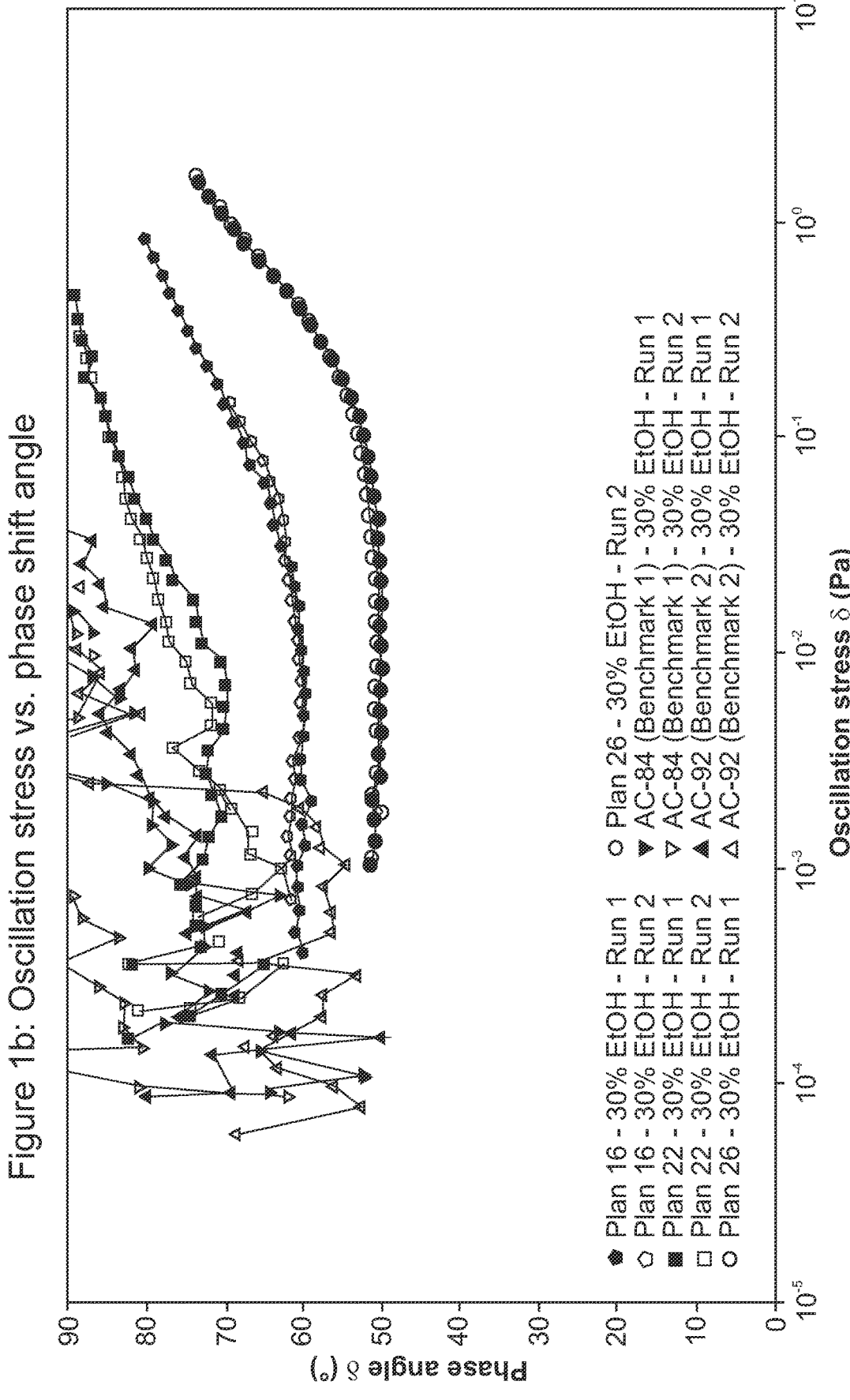
Figure 1b: Oscillation stress vs. phase shift angle

COSMETIC COMPOSITION CONTAINING AN EXTRACT FROM OPUNTIA FICUS INDICA

CROSS-REFERENCE TO RELATED APPLICATIONS

This application is a national stage application (under 35 U.S.C. § 371) of PCT/EP2020/080712, filed Nov. 2, 2020, which claims benefit of European Application No. 19206753.6, filed Nov. 1, 2019, both of which are incorporated herein by reference in their entirety.

The invention relates to a cosmetic composition containing a hydrocolloidal extract of *Opuntia ficus indica*, wherein mucilages are selectively enriched. Furthermore, the invention relates to a hydrocolloidal extract of *Opuntia ficus indica*, a process for its preparation, and its use.

The pear cactus (*Opuntia ficus indica*) is a plant species of the *Opuntia* genus and belongs to the cactus family (Cactaceae). Originally, opuntias, also called tuna cacti, come from the American continent, where both hardy and non-hardy species occur between Canada and southern Argentina and are now also native to Europe. The pear cactus should not be confused with the prickly pear, the latter referring to the fruit. *Opuntia ficus indica* has many uses, such as fruit cultivation, fodder, vegetable, etc.

Weleda AG researches beneficial natural plant substances for cosmetics using modern methods and in conjunction with anthroposophical methods.

As the largest human organ, the skin performs numerous vital functions. For example, it protects against cold, heat, radiation, the effects of chemical substances and pathogens. If the skin no longer sufficiently fulfils this barrier function, local irritations or even whole-body complaints can occur.

As a barrier organ of the human organism, the skin, especially the epidermis, is particularly subject to external influences. This barrier function is maintained by skin lipids, among other things. These epidermal lipids, such as glycosphingolipids, ceramides, sterols and sterol esters, fatty acids, triglycerides, n-alkanes or various polar lipids, are released in the keratinisation process.

In an optimal state of the skin, there is a balanced ratio of skin lipids and skin moisture. This balance determines important properties of the skin, such as penetration capacity, water-binding capacity, elasticity, regenerative capacity or resistance to environmental influences and noxious substances of various kinds. The maintenance of skin moisture is a cosmetic challenge for the prevention of ageing, especially the formation of wrinkles.

In the prior art, DE 20 2016 008 641 U1 discloses the potential suitability of *Opuntia ficus indica* for use as a topical skincare composition.

WO 2009/058613 discloses a topical composition containing an *Opuntia ficus indica* extract (claims 5, 8 and 15) which stimulates hyaluronic acid production and can be used as a moisturiser. It is further described that the *Opuntia ficus indica* extract can be obtained in various ways.

KR 20030023398 A discloses a topical composition comprising an *Opuntia ficus indica* extract, but no hydrocolloidal extract is obtained or disclosed because an excess amount of ethanol is added after a first aqueous extraction, but before maceration followed by filtration (Example 1 therein).

Furthermore, the cosmetic suitability of prickly pear seed oil is described in EP 3 102 181 B1.

However, the special role of the natural mucilages of *Opuntia ficus indica* in cosmetics, which can preferably be obtained from plant parts or plant cells, but preferably from the cladodes, is not recognised in the prior art. In particular, the beneficial effect of the mucilages for hydration or water binding with the formation of a hydrocolloidal extract is not recognised in the prior art.

*Opuntia ficus indica* extracts are known in liquid form or as dry extracts (powdered). However, these are simply made from pressed juice of fresh cladodes. This cladode juice is microbiologically stabilised by pH regulation or addition of preservatives or by conversion into a powder form (with or without carrier). However, this pressed juice contains only small amounts of mucilages and therefore has a low viscosity in the fluid state. Therefore, no hydrocolloidal extract is obtained. The physical properties and efficacy profiles of two commercial benchmarks, both made from pressed juice, are compared with the subject matter of the invention in the examples.

According to the invention, mucilages from *Opuntia ficus indica* are those which consist with the highest proportion of differently structured high-molecular polysaccharides and can contain a proportion of polyphenols, phenols and other secondary plant constituents. According to the invention, their complex, high-molecular structures are particularly suitable for absorbing high amounts of water, so that mucilage-like colloids and gels or hydrocolloids can be formed. In addition, these mucilages have an anti-irritant, mucous membrane-protecting and anti-inflammatory effect on the organism.

It is therefore the object of the present invention to provide a cosmetic composition for topical use from *Opuntia ficus indica* mucilages, and also a process for preparing a hydrocolloidal extract of *Opuntia ficus indica*, wherein the *Opuntia ficus indica* mucilages can be enriched.

Surprisingly, the inventors were able to determine that the pure hydrocolloidal extract with enriched proportions of mucilages provides a particularly beneficial cosmetic effect and contributes intensively and sustainably to skin moisturisation in a natural way. Due to the targeted enrichment of mucilages, a high level of hydration can be advantageously achieved with the formation of a hydrocolloidal extract.

The object is therefore achieved by a process for preparing a hydrocolloidal extract from plant material of *Opuntia ficus indica*, wherein a.) an aqueous or preferably aqueous-alcohol extract with a maximum of 40% (m/m) alcohol is prepared from plant material of *Opuntia ficus indica*, wherein the alcohol can be a C1-C4 or C1-C3 alcohol, but is preferably ethanol (C2), b.) the obtained extract is treated under heat at 60-90 degrees Celsius for one hour or longer, c.) is macerated and filtered after cooling.

BRIEF DESCRIPTION OF FIGURES

FIG. 1*a* shows, on the basis of the extracts prepared according to the invention, designated as Plan 16, Plan 22 and Plan 26, a behaviour of a non-Newtonian fluid in comparison to the commercially available benchmark extracts of *Opuntia ficus indica* cladodes (samples AC-84 (Benchmark 1 (supra) and AC-92 (Benchmark 2 (supra)), while samples AC-84 and AC-92 show a Newtonian fluid behaviour (measurement under normal conditions).

FIG. 1*b* shows, by means of an oscillation measurement technique, that the phase shift angle in the mucilage-rich hydrocolloidal extracts (samples: Plan 16, Plan 22 and Plan 26) is reduced in the broad oscillation range and is constant at 45°-65°, which indicates that the hydrocolloidal network structures tend to be elastic and structured.

In a preferred embodiment, the maceration can take place for at least 7 hours or for days before filtration. Furthermore, a new maceration can take place after filtration. The maceration can also be carried out as a movement maceration, wherein the movement is preferably effected with the aid of stirring.

The filtration according to step c.) is preferably carried out with one or more sieves, wherein the sieve openings are preferably 60-300 μm. This allows the retention of solids so that a pure and stable hydrocolloidal extract of *Opuntia ficus indica* can be obtained.

Step c.) can be repeated once or several times, if necessary, until the hydrocolloidal extract is completely formed, so that all mucilages have been exhaustively transferred into the extract.

In a particularly preferred embodiment, the proportion of alcohol, in particular ethanol, is at most 35% (m/m) (35:65) in the alcohol-aqueous, in particular ethanolic-aqueous extract, preferably 30% (30:70) or even 20% (20:80) and less, but preferably more than 10%.

Furthermore, C1-C4 or C1-C3 alcohols can be used, such as methanol (C1), propanol (C3), butanol (C4), but preferably ethanol (C2). Furthermore, it is preferred that the ethanol preferably used contains 94.00% m/m ethanol.

Likewise, alcohol-aqueous extracts can be made with polyvalent alcohols, in particular divalent and trivalent alcohols, especially those such as glycol, 1,2-propanediol, glycerol or polyol.

The inventors were able to determine that the mucilages already precipitate disadvantageously from 30% alcohol, in particular ethanol, and cannot be transferred or can only be partially transferred into the hydrocolloidal extract. Furthermore, a purely aqueous extraction is possible, but the aforementioned alcohol-aqueous extraction is preferred according to the invention, so that the mucilages can be completely transferred into the hydrocolloidal extract in a time-efficient manner and, in particular, those portions of mucilages can be transferred which contain secondary plant constituents (polyphenols, phenols, flavonoids, etc.), also in combination with polysaccharides. In addition, it is disadvantageous that the aqueous extract cannot be subsequently loaded, e.g. with alcohol for preservation, since the mucilages precipitate.

In the maceration according to step c.), the plant material is placed for a certain time in a liquid, in particular in the existing liquid, but preferably in an aqueous-ethanolic liquid (supra), wherein the macerate (liquid) comprises the hydrocolloidal extract.

In a preferred embodiment, the plant material is dried and comminuted in step a.). Flowers are preferably not to be considered as plant material and, if necessary, are to be excluded. However, the use of cladodes from *Opuntia ficus indica*, in particular dried cladodes, is particularly preferred.

In a further preferred embodiment, the heat treatment according to step b) can be carried out with stirring.

Furthermore, it is preferred that the heat treatment according to step b) is carried out at 65-85 degrees Celsius, in particular at 70 to 80 degrees Celsius, in particular 80 degrees Celsius.

Furthermore, it is preferred that the heat treatment according to step b) takes place within 1 h.

The hydrocolloidal extract with enriched content of mucilages according to the invention shows an advantageous non-Newtonian flow behaviour as a function of shear rate to viscosity as well as oscillation measurements, see the examples and FIGS. 1*a* and 1*b*.

This rheological behaviour is clearly due to the hydrocolloidal properties of the mucilage-rich extract of a non-Newtonian fluid.

Due to the increased mucilage content, the extract according to the invention exhibits the non-Newtonian flow behaviour explained above or is a non-Newtonian fluid. The rheological properties can be used as evidence, namely as a differentiating and quality feature for the particular suitability as a humectant, since the hydrocolloidal character of the extract formed in accordance with the invention is responsible for its water-binding capacity.

The process according to the invention allows the advantageous enrichment of mucilages, which in principle comprise the inherent polysaccharides contained natively in *Opuntia ficus indica*. These are extract-inherent polysaccharides, which are released from the plant substance due to the process according to the invention and are enriched as mucilage, and do not have to be added.

Therefore, the invention also relates to an *Opuntia ficus indica* extract, in particular a hydrocolloidal extract obtainable from the process according to the invention.

In a further embodiment, the hydrocolloidal extract according to the invention has a viscosity, in particular a zero shear viscosity, of 5.55 mPa*s and more, in particular 25.4 mPa*s and more.

In a further embodiment, the hydrocolloidal extract according to the invention has a viscosity vs. shear rate of 4.51 mPa*s at $10E2 \ s^{-1}$ and more, in particular 8.1 mPa*s at $10E2 \ s^{-1}$ and more.

In a further embodiment, the hydrocolloidal extract according to the invention has a viscosity vs. shear rate of 3.19 mPa*s at $10E3 \ s^{-1}$ and more, in particular 4.44 mPa*s at $10E3 \ s^{-1}$ and more.

A cosmetic product according to the invention therefore has no additional sugars, such as maltodextrin or the like, but has a hydrocolloidal extract with unique mucilages containing in particular polysaccharides with excellent properties for maintaining skin moisture (moisturising). Consequently, according to the invention, an excellent skin-moisture-binding and -maintaining agent is obtained. Moisturisation of the skin is essential in all age groups. Therefore, it is particularly advantageous for substances and preparations to have a high level of moisture enrichment. Reduced skin hydration leads to undesirable skin conditions that can, among other things, accelerate the ageing process.

Therefore, the invention also relates to an anti-ageing product comprising the hydrocolloidal extract according to the invention.

In a further embodiment, the cosmetic or dermatological preparation for topical use according to the invention can be in the form of a gel, a spray, a cream or a lotion, wherein aqueous systems are preferably used.

Emulsifiers can advantageously be selected from the group of non-ionic, anionic, cationic or amphoteric emulsifiers.

Preferred emulsifiers according to the invention are naturally occurring emulsifiers, which include, for example, beeswax, lanolin, lecithin and sterols, among others, which can also be used in the preparation of a composition according to the invention.

The cosmetic compositions according to the invention can further contain cosmetic excipients as commonly used in such preparations, e.g. antioxidants, radical catchers, preservatives, bactericides, perfumes, dyes, pigments having a colouring effect, thickening agents, surfactants, emollients, or other common ingredients of a cosmetic formulation, such as alcohols, polyols, polymers, foam stabilisers, electrolytes, organic solvents.

In a further particular embodiment, the composition according to the invention preferably consists of ingredients that are naturally occurring or near-natural, or nature-identical.

In a further preferred embodiment, the cosmetic composition according to the invention additionally comprises a moisturiser, in particular selected from the group of hyaluronic acid, glycerol, aloe vera barbadensis juice, betaine, sorbitol, xylitol, 1,2-propylene glycol, polyalcohols.

In a further embodiment, the cosmetic composition according to the invention can be applied to a solid carrier, such as wet wipes.

The following exemplary embodiments and figures serve to explain the invention without limiting the invention to these examples.

EXAMPLE 1

The moisturising properties of the extract of *Opuntia ficus indica* cladodes were put to the test in a comparative trial with commercially available extracts (benchmarks) in an in-vivo study on 29 volunteers. The following market products were used for the comparison: Benchmark 1—*Opuntia* Biocomplex SH from Bionap® in powder form and Benchmark 2—liquid extract Aquapuntia® from Biocosmethic. Both benchmarks are produced from the juice of fresh *Opuntia ficus indica* cladodes and only one pressed juice is obtained in each case. The various products were incorporated into a cosmetic model formulation according to the recommendations for the use concentration from the respective manufacturers, and due to its composition had no moisturising properties and was additionally used as a placebo.

| Ingredient (INCI) | Percentage by weight |
|---|---|
| Aqua | ad 100% |
| Glyceryl stearate citrate | 7.00% |
| Caprylic/Capric triglyceride | 6.00% |
| Octyldodecanol | 4.00% |
| Cetyl alcohol | 0.86% |
| Benzyl Alcohol | 0.10% |
| Benzoic Acid | 0.10% |
| Sorbic acid | 0.05% |
| Citric acid | 0.05% |

The moisturising properties of the test formulations were determined with a corneometer (Corneometer CM® 825 (Courage & Khazaka electronic) using capacitive determination of the AC resistance. The determined values correlate with the skin moisture of the upper skin layers. The significance of the results was evaluated by p-value. The model formulation was mixed with 2% of the mucilage-enriched *Opuntia ficus indica* extract according to the invention and compared with the same concentration of Benchmark 1 and Benchmark 2. Table 1 shows the increase in moisture (hydration) of the skin (layers) after application within 2 h, 4 h and 24 h on the forearm skin of the test subject.

TABLE 1

| | Increase in hydration | | |
|---|---|---|---|
| | after 2 h | after 4 h | after 24 h |
| Hydrocolloidal extract with enriched mucilage content | 13% | 14% | 8% |
| Benchmark 1 | 5% | 5% | not significant |
| Benchmark 2 | 6% | 5% | −4% |

The results show that the cosmetic model formulations exhibit a significant increase in hydration after 2 h, 4 h and 24 h; in particular the increase is strongly increased when a mucilage-enriched hydrocolloidal extract according to the invention is added. The commercially available benchmarks show a significantly reduced or a non-significant or even a negative effect at the same use concentration.

EXAMPLE 2

The hydrocolloidal character of the liquid extract of *Opuntia ficus indica* according to the invention correlates with the sufficient content of mucilages extracted from the cladodes and is reflected in both the viscosity and the flow behaviour of the extract. These properties were tested in a comparative trial with commercially available extracts (benchmarks). The following market products were used for the comparison: Benchmark 1—*Opuntia* Biocomplex SH from Bionap® in powder form and Benchmark 2—liquid extract Aquapuntia® from Biocosmethic. The dry extract (Benchmark 1) additionally contains maltodextrin as a carrier and is recommended by the manufacturer for use in topical formulations at 2-5% w/w. For the comparison, aqueous solutions of Benchmark 1 were freshly prepared with 2%, 3% and 5% of the dry extract. Benchmark 2 was used directly in its delivery form as a liquid extract.

The comparative tests were carried out with the aid of a flow cup. This device comprises a conical container with a discharge opening in the bottom including a defined diameter, mounted on a 3-legged frame. The flow cup is filled to the brim with the test liquid while the bottom opening remains manually closed. As soon as the bottom opening is opened, the run-out time of the test liquid until the cup is emptied is measured. Experimentally determined run-out times correlate with the rheological character of the extracts, which are described in Example 3.

TABLE 2

| | Run-out times of the Opuntia ficus indica extracts | | | | |
|---|---|---|---|---|---|
| | Extract | | | | |
| | Opuntia ficus indica extract prepared in accordance with the invention | Benchmark 1 2% solution in water | Benchmark 1 3% solution in water | Benchmark 1 5% solution in water | Benchmark 2 |
| Run-out time | min. 20 s | 10 s | 10 s | 10 s | 10 s |

The run-out time of benchmarks 1 and 2 is considerably shorter than the run-out time of the extract according to the invention. This indicates a significantly lower mucilage content of the two benchmarks tested. This is due to the fact that mechanical juice pressing does not exhaustively extract mucilage and no hydrocolloidal extract is obtained.

Extraction tests on dried cladodes also show that the addition of 30% ethanol to an extract rich in mucilage leads to visible, flake-like precipitations. When adding 30% ethanol to benchmarks 1 and 2, only a homogeneous turbidity was observed, leading to sediment formation after 24 h. The absence of flakes rules out a hydrocolloidal network of the benchmarks and confirms that benchmarks 1 and 2 at most have small amounts to traces of mucilages.

EXAMPLE 3

Viscosity and Shear Rate Measurement with a Rheometer (DHR2, TA Instruments)

FIG. 1a shows, on the basis of the extracts prepared according to the invention, designated as Plan 16, Plan 22 and Plan 26, a behaviour of a non-Newtonian fluid in comparison to the commercially available benchmark extracts of *Opuntia ficus indica* cladodes (samples AC-84 (Benchmark 1 (supra)) and AC-92 (Benchmark 2 (supra)), while samples AC-84 and AC-92 show a Newtonian fluid behaviour (measurement under normal conditions).

TABLE 3

| | Viscosity vs. shear rate | | | | | |
| --- | --- | --- | --- | --- | --- | --- |
| | Viscosity (mPa · s) at 10E2 s − 1 | | | Viscosity (mPa · s) at 10E3 s − 1 | | |
| T Sample | Run 1 | Run 2 | Mean value | Run 1 | Run 2 | Mean value |
| AC-84 | 2.24 | 2.26 | 2.25 | 2.34 | 2.36 | 2.35 |
| AC-92 | 1.45 | 1.40 | 1.43 | 1.71 | 1.66 | 1.68 |
| Plan 16 | 8.10 | 8.67 | 8.38 | 4.44 | 4.78 | 4.61 |
| Plan 22 | 4.51 | 4.61 | 4.56 | 3.19 | 3.28 | 3.24 |
| Plan 26 | 17.6 | 17.4 | 17.5 | 7.50 | 7.40 | 7.45 |

FIG. 1b shows, by means of an oscillation measurement technique, that the phase shift angle in the mucilage-rich hydrocolloidal extracts (samples: Plan 16, Plan 22 and Plan 26) is reduced in the broad oscillation range and is constant at 45°-65°, which indicates that the hydrocolloidal network structures tend to be elastic and structured. The rheological properties, especially the non-Newtonian flow behaviour, are clearly different from the commercially available *Opuntia ficus indica* extracts (samples AC-84 (benchmark 1 (supra)) and AC-92 (benchmark 2 (supra)). Samples AC-84 and AC-92 show a much lower zero shear viscosity at the exposed oscillations (measurement under normal conditions).

TABLE 4

| | Zero shear viscosity (mPa · s) | | |
| --- | --- | --- | --- |
| Sample | Run 1 | Run 2 | Mean value |
| AC-84 | 2.23 | 2.53 | 2.38 |
| AC-92 | 1.52 | 1.74 | 1.63 |

8

TABLE 4-continued

| | Zero shear viscosity (mPa · s) | | |
| --- | --- | --- | --- |
| Sample | Run 1 | Run 2 | Mean value |
| Plan 16 | 25.4 | 27.5 | 26.4 |
| Plan 22 | 5.97 | 5.55 | 5.76 |
| Plan 26 | 73.4 | 104 | 88.9 |

The invention claimed is:

1. A process for preparing a hydrocolloidal extract from *Opuntia ficus indica*, characterised in that
   a.) an aqueous-alcohol extract with a maximum of 40% (m/m) alcohol is prepared from plant material of *Opuntia ficus indica*,
   b.) the obtained extract is treated under heat at 60-90 degrees Celsius for one hour or longer,
   c.) is macerated and filtered after cooling.

2. The process according to claim 1, wherein the alcohol is a C1-C4 alcohol.

3. The process according to claim 1, wherein the alcohol is a ethanol.

4. The process according to claim 1, wherein the alcohol is a polyvalent alcohol.

5. The process according to claim 1, wherein the alcohol is a polyvalent alcohol selected from the group of glycol, 1,2-propanediol, glycerol or polyol.

6. The process according to claim 1, wherein the aqueous-alcohol extract is prepared with a maximum of 30% (m/m) alcohol.

7. The process according to claim 1, wherein the aqueous-alcohol extract is prepared with a maximum of 20% (m/m) ethanol.

8. The process according to claim 1, wherein the plant material of *Opuntia ficus indica* is cladodes.

9. A process for preparing a hydrocolloidal extract from *Opuntia ficus indica*, characterised in that
   a.) an aqueous or aqueous-alcohol extract with a maximum of 40% (m/m) alcohol is prepared from plant material of *Opuntia ficus indica*,
   b.) the obtained extract is treated under heat at 60-90 degrees Celsius for one hour or longer,
   c.) is macerated and filtered after cooling,
   wherein the filtration in step c.) is carried out with one or more sieves, wherein the sieve openings are 60-300 μm.

10. A process for preparing a hydrocolloidal extract from *Opuntia ficus indica*, characterised in that
   a.) an aqueous or aqueous-alcohol extract with a maximum of 40% (m/m) alcohol is prepared from plant material of *Opuntia ficus indica*,
   b.) the obtained extract is treated under heat at 60-90 degrees Celsius for one hour or longer,
   c.) cooling the heat treated extract, then
   d.) macerating and filtering the extract,
   wherein the macerating is carried out with stirring.

* * * * *